United States Patent [19]

Kourai et al.

[11] Patent Number: 4,826,924

[45] Date of Patent: May 2, 1989

[54] ANTIBACTERIAL POLYMER

[75] Inventors: Hiroki Kourai; Yoshio Yabuhara, both of Tokushima, Japan

[73] Assignee: Otsuka Kagaku Kabushiki Kaisha, Osaka, Japan

[21] Appl. No.: 231,425

[22] Filed: Aug. 12, 1988

Related U.S. Application Data

[63] Continuation-in-part of Ser. No. 180,132, Apr. 11, 1988.

[30] Foreign Application Priority Data

Apr. 17, 1987 [JP] Japan ................................. 62-96042

[51] Int. Cl.$^4$ ........................................... C08F 236/18
[52] U.S. Cl. ............................. 525/331.3; 525/331.4; 525/382; 523/122; 524/519; 424/78
[58] Field of Search ................... 525/331.3, 331.4, 382

[56] References Cited

U.S. PATENT DOCUMENTS 2,992,544  7/1961  McMaster ........................ 525/331.4

Primary Examiner—C. Warren Ivy
Assistant Examiner—Alex H. Walker
Attorney, Agent, or Firm—Armstrong, Nikaido Marmelstein & Kubovcik

[57] ABSTRACT

An antibacterial polymer containing a repeating unit of the formula

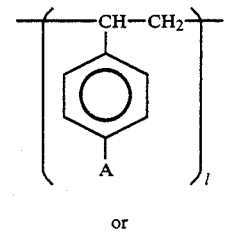

or

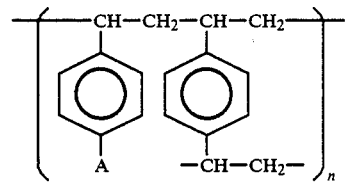

wherein A, l and n are defined in the specification.

1 Claim, No Drawings

ANTIBACTERIAL POLYMER

CROSS-REFERENCE TO RELATED APPLICATION

This application is a continuation in part of co-pending application Ser. No. 180,132, filed Apr. 11, 1988.

The present invention relates to an antibacterial polymer having quaternary nitrogen atoms(s). The polymer is widely used for germicide for pool water, drinking water and cooling water, slime control agent, floor material, wall material, ceiling material or like building materials, agricultural materials, etc.

Among the conventional antibacterial compounds, a low-molecular one is used as admixed with a material constituting various products. In this case, the effective component having antibacterial activity is apt to release outwardly or to separate downward, consequently the antibacterial compound has a defect of being low in durability of antibacterial action.

Therefore, high-molecular compounds having antibacterial activity are developed to solve the above problems but sufficient results have not yet achieved.

An object of the invention is to provide an antibacterial polymer having an excellent antibacterial activity and durability in the activity.

The above and other objects of the invention will become apparent from the following description.

The present invention provides an antibacterial polymer containing a repeating unit of the formula

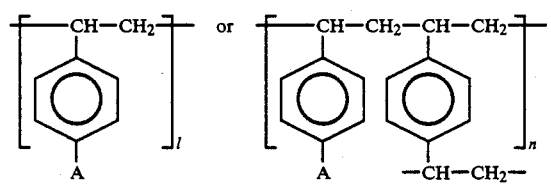

wherein A is

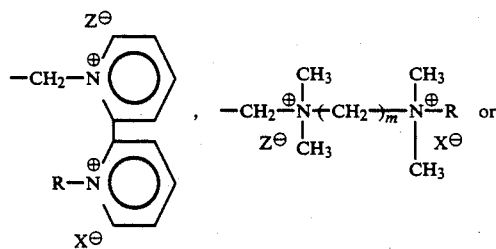

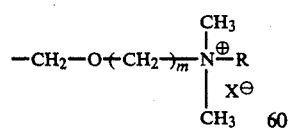

$l$ is 20 to 2000, n is a number of at least 1000, X and Z are the same or different and are in anion, R is alkyl group having 6 to 18 carbon atoms, m is an integer of 2 to 10.

In the antibacterial polymer of the present invention, the long-chain alkyl group R has preferably 6 to 18 carbon atoms but alkyl group of 8, 10 or 12 carbon atoms is more preferable in the viewpoint of antibacterial activity. Anions are not particularly limited and include $Br^-$, $Cl^-$, $I^-$, $NO_3^-$, $CH_3COO^-$ and $SO_4^{2-}$. Preferably $l$ is 20 to 2000, n is a number at least 1000 and m is an integer of 2 to 10.

The antibacterial polymer of the present invention is characterized in that the quaternary nitrogen atom is apart from the polymer main chain, the polymer is insoluble and high in antibacterial activity.

The antibacterial polymer of the present invention is preferably a spherical particle having a diameter of 3 to 500 μm. The present polymer is used as packed in a column, as suspended in water or in the form of a sheet obtained with use of a blend of the present polymer and other polymer.

The antibacterial polymer of the present invention exhibits wide antibacterial spectra over Gram positive bacteria and Gram negative bacteria. Further, the present polymer shows growth preventing effect over mould.

The following is an example of preparation of the antibacterial polymer of the present invention by use of reaction equations.

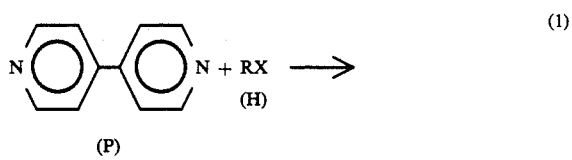

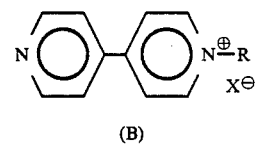

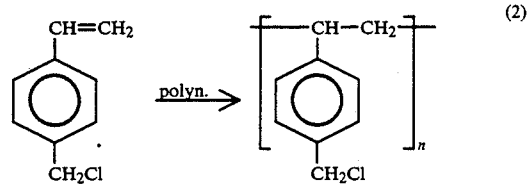

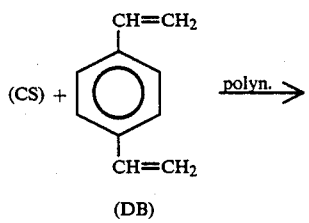

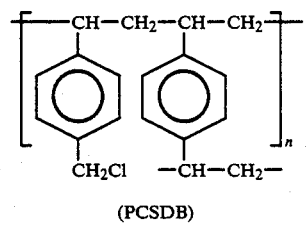

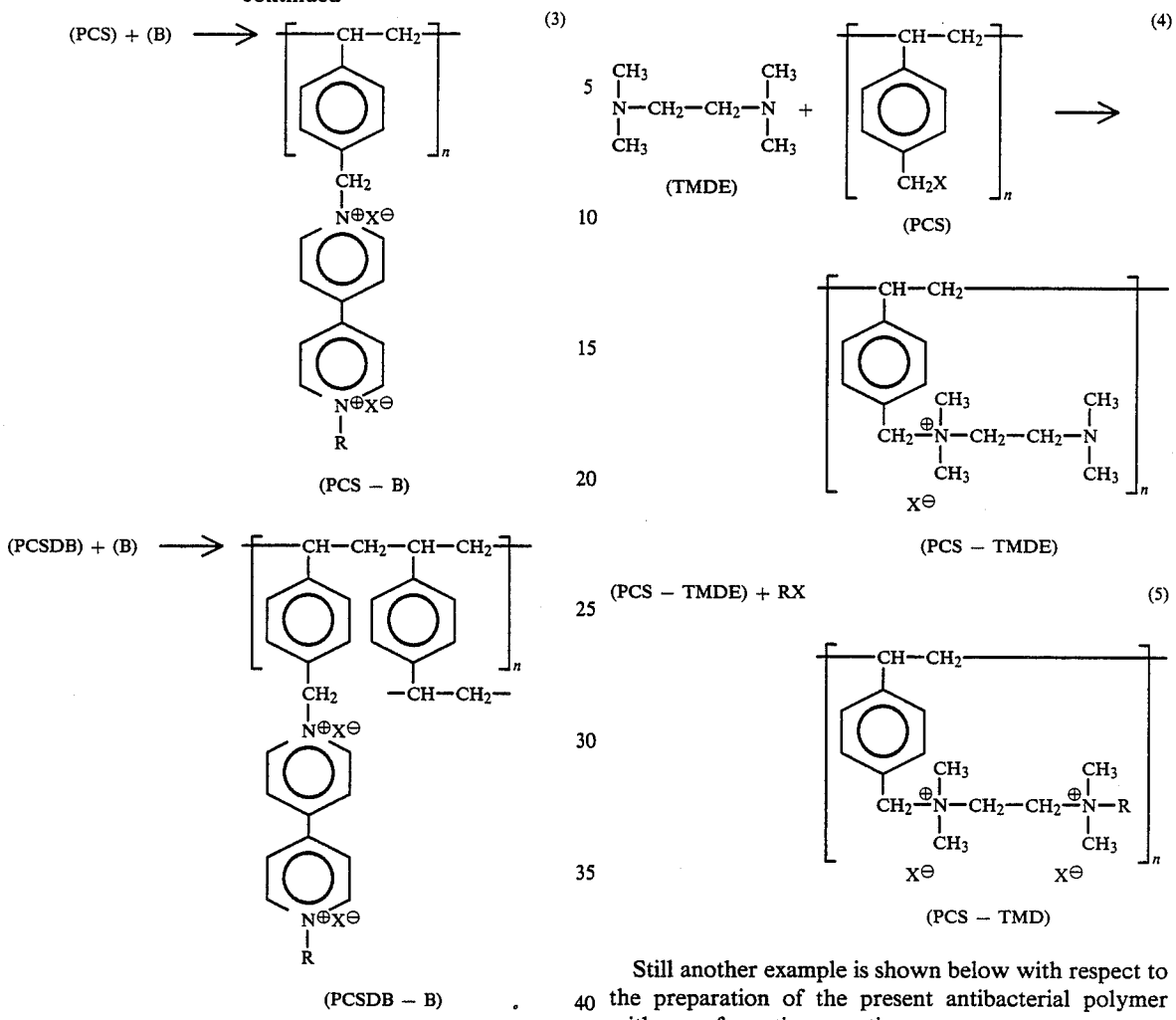

In the above reaction equation (1), the compound (P) is used usually in an amount of 1.0 to 2.5 moles, preferably about 1.1 to 2.1 moles per mole of the compound (H). The reaction is conducted preferably in a solvent and the reaction temperature is preferably about 60° to 110° C. The product (B) can be purified by a method such as concentration, distillation and recrystallization. The polymerization shown by the equation (2) can be carried out by a usual method such as suspension polymerization, solution polymerization and bulk polymerization. The obtained polymer is purified by a method such as reprecipitation and washing. In the reaction shown by the equation (3), the compound (B) is used usually in an amount of about 0.02 to 0.15 equivalent, preferably about 0.05 to 0.10 equivalent per equivalent of chlorine of the compound (PCS) or (PCSDB). The reaction is conducted preferably in an organic solvent and generally conducted at a temperature of about 60° to 100° C. The obtained (PCS-B) or (PCSDB-B) can be purified by a method such as reprecipitation and washing. Compounds wherein A is other than the above can be prepared in the similar reaction to the above.

The following is an another example of preparation of the antibacterial polymer of the present invention by use of reaction equations.

Still another example is shown below with respect to the preparation of the present antibacterial polymer with use of reaction equations.

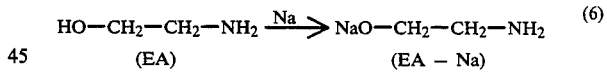

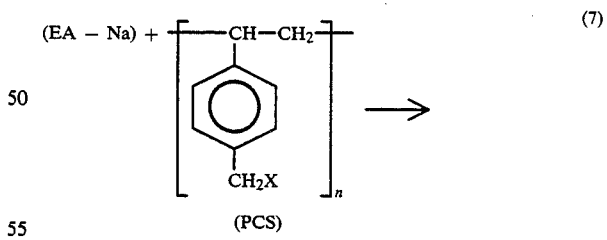

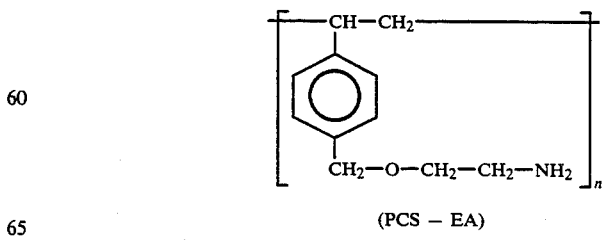

-continued

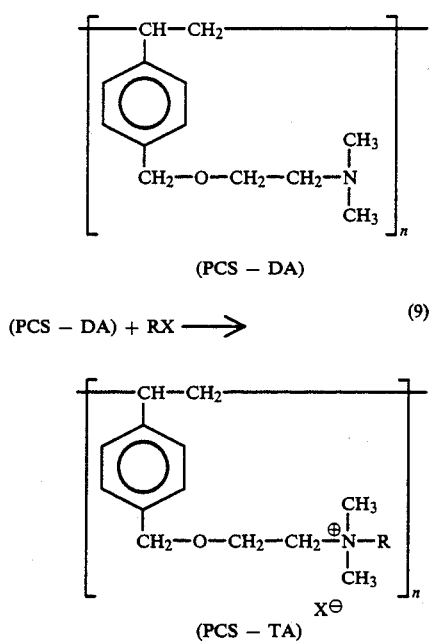

(PCS — DA)

$$(PCS - DA) + RX \longrightarrow \quad (9)$$

(PCS — TA)

The antibacterial polymer of the present invention has an excellent antibacterial activity and exhibits wide antibacterial spectra. The polymer is widely used for germicide for pool water, drinking water and cooling water or slime control agent. Further, the polymer is added to a synthetic resin and the like and is effectively used for preventing the growth of bacteria and mould in building materials, agricultural materials, etc.

The present invention will be described in detail by showing examples and test examples.

EXAMPLE 1

Into a 300 ml round-bottom flask equipped with a stirrer, reflux condenser, nitrogen-introducing tube and dropping funnel were placed 100 ml of ethyl alcohol and 31.2 g (0.2 mole) of 4,4'-bipyridyl and thereto added dropwise 24.9 g (0.1 mole) of lauryl bromide through the dropping funnel over a period of 2 hours while introducing dry nitrogen and heating on an oil bath of 90° C. After heating and stirring for 18 hours, the solvent was removed and the residue was recrystallized from methanol/acetone to obtain 55 g of N-lauryl-4,4'-pyridylpyridinium bromide (hereinafter referred to as "B"). The similar reactions were conducted with respect to other alkyl halides.

A homopolymer (PCS) of p-chloromethylstyrene (CS) was prepared by a conventional suspension polymerization. The polymer was washed with hot acetone to remove an unreacted monomer.

In 800 ml of methanol, 10 g of the above (B) and 200 g of the polymer PCS were reacted at 60° C. for 50 hours to obtain 208.3 g of the antibacterial polymer (PCS-B).

EXAMPLE 2

A copolymer (PCSDB) of CS and divinylbenzene (DB) was prepared by polymerization reaction in the same manner as in Example 1. The polymer was washed with hot acetone to remove an unreacted monomer.

In 800 ml of ethanol, 5 g of the above (B) and 200 g of the polymer PCSDB were reacted at 70° C. for 20 hours to obtain 204.5 g of the antibacterial polymer (PCSDB-B).

Each of the above antibacterial polymers had a formation rate of quaternary ammonium of about 90% by analysis with use of a solution of Bromophenol Blue (BPB) in methanol.

EXAMPLE 3

Into a 300 ml round-bottom flask equipped with a stirrer, reflux condenser, nitrogen-introducing tube and dropping funnel were placed 290 g (4.8 moles) of nitromethane and 13.5 g (0.086 mole) of 2,2'-bipyridyl and thereto added dropwise 44.7 g (0.18 mole) of lauryl bromide through the dropping funnel over a period of 2 hours while introducing dry nitrogen and heating on an oil bath of 110° C. After heating and stirring for 5 hours, the solvent was removed and the residue was recrystallized from ethanol/acetone to obtain 12 g of N-lauryl-2,2'-pyridylpyridinium bromide (hereafter referred to as "2,2'-BPQ-$C_{12}$"). The similar reactions were conducted with respect to other alkyl halides.

In 800 ml of methanol, 10 g of the above (2,2'-BPQ-$C_{12}$) and 200 g of the polymer PCS obtained in Example 1 were reacted at 60° C. for 50 hours to obtain 207.2 g of the antibacterial polymer (2,2'-BPCQ-$C_{12}$).

TEST EXAMPLE 1

An antibacterial spectrum was measured in the following manner.

To a 500 ml-Erlenmeyer flask which was placed in a constant temperature bath of 30° C. equipped with a shaker was added 20 mg of the antibacterial polymer (PCSDB-B). To the flask was added 100 ml of bacteria suspension listed in Table 1 ($6 \times 10^8$ cells of bacteria) of 30° C. and the mixture was shaked immediately. Each 1 ml of the mixture was sampled 0, 2 and 5 minutes after the addition of the bacteria suspension. The sample was immediately diluted with sterile isotonic sodium chloride solution in 10, 100 and 100 times in dilution rate and then spread on nutrient agar plates.

Survival rate (%) was determined by measuring the survived bacteria in the colony after cultivation at 37° C. for 24 hours.

The results are given in Table 1.

TABLE 1

| | Survival rate (%) | |
|---|---|---|
| Bacteria | after 2 min. | after 5 min. |
| Gram negative bacteria | | |
| Pseudomonas aeruginosa IFO 3080 | 0.07 | 0 |
| Pseudomonas aeruginosa ATCC 10145 | 0 | 0 |
| Escherichia coli K12 OUT 8401 | 0 | 0 |
| Escherichia coli IFO 3301 | 0 | 0 |
| Proteus vulgaris Ox$_{19}$RIMD | 38.52 | 5 |
| Gram positive bacteria | | |
| Staphylococcus aureus NIHJ-JCI | 0 | 0 |
| Bacillus subtilis var. niger OUT 4380 | 0 | 0 |
| Bacillus cereus IFO 3001 | 0 | 0 |
| Bacillus megaterium IFO 3003 | 28.61 | 0 |

TEST EXAMPLE 2

Five kinds of sheets were prepared by mixing the components listed in Table 2 under the following conditions.

(a) mixing roll; D=10 in. 16 rpm
(b) roll temperature+time; 140°~145° C.×5 min.
(c) thickness of sheet; 0.5 mm Each of the obtained sheets was checked for antimicrobial activity against mould according to JIS Z2911. The results were shown in Table 3.

TABLE 2

| No. | 1 | 2 | 3 | 4 | 5 |
|---|---|---|---|---|---|
| PVC (P = 1100) | 100 | 100 | 100 | 100 | 100 |
| Plasticizer (DOP) | 48 | 48 | 48 | 48 | 48 |
| Stabilizer (Mark OF-23) | 2 | 2 | 2 | 2 | 2 |
| PCS-B | — | 0.10 | 0.15 | 0.20 | 0.30 |
| Content of PCS-B (wt. %) | 0.00 | 0.067 | 0.100 | 0.133 | 0.200 |

TABLE 3

| Fungi | No. | \multicolumn{6}{c}{Days} |
|---|---|---|---|---|---|---|---|

| Fungi | No. | 5 | 10 | 15 | 20 | 25 | 28 |
|---|---|---|---|---|---|---|---|
| Aspergillus niger IFO 4414 | 1 | + | +s | +s | +s | +s | +s |
|  | 2 | — | — | — | — | + | + |
|  | 3 | — | — | — | — | — | + |
|  | 4 | — | — | — | — | — | — |
|  | 5 | — | — | — | — | — | — |
| Penicillium citrinum IFO 6026 | 1 | + | +s | +s | +s | +s | +s |
|  | 2 | — | — | — | — | + | + |
|  | 3 | — | — | — | — | — | + |
|  | 4 | — | — | — | — | — | — |
|  | 5 | — | — | — | — | — | — |
| Rhizopus stolonifer IFO 5411 | 1 | + | +s | +s | +s | +s | +s |
|  | 2 | — | — | + | + | + | + |
|  | 3 | — | — | — | — | + |  |
|  | 4 | — | — | — | — | — | — |
|  | 5 | — | — | — | — | — | — |

In Table 3, Nos. 1~5 correspond respectively 0, 0.067, 0.100, 0.133 and 0.200 wt.% of (PCS-B) to PVC.
+; mycelial growth
s; sporulation
—; no growth

TEST EXAMPLE 3

The antibacterial polymer (2,2'-BPCQ-$C_{12}$) was checked for antibacterial activity with use of 10 mg thereof in the same manner as in Test Example 1. The results were shown in Table 4.

TABLE 4

| Bacterium | Survival rate (%) | | |
|---|---|---|---|
|  | after 10 min. | after 20 min. | after 30 min. |
| Escherichia coli K12 OUT8401 | 8.0 | 0 | 0 |

EXAMPLE 4

Into a 100 ml flask were placed 10 g of the polymer PCS obtained in Example 1, 3.8 g (0.033 mole) of N,N,N',N'-tetramethyldiaminoethane (TMDE) and 50 ml of ethanol. The mixture was reacted at 90° C. for 36 hours.

To the mixture was added 10 g (0.04 mole) of lauryl bromide and the mixture was reacted at 90° C. for 36 hours to obtain 22.5 g of the antibacterial polymer (PCS-TMD).

The polymer had a formation rate of quaternary ammonium of about 89% by analysis with use of a solution of Bromophenol Blue (BPB) in methanol.

TEST EXAMPLE 4

The antibacterial polymer (PCS-TMD) was checked for antibacterial activity with use of 20 mg thereof in the same manner as in Test Example 1. The results were shown in Table 5.

TABLE 5

| Bacteria | Survival rate (%) | |
|---|---|---|
|  | after 2 min. | after 5 min. |
| Gram negative bacteria | | |
| Pseudomonas aeruginosa IFO 3080 | 0.05 | 0 |
| Pseudomonas aeruginosa ATCC 10145 | 0 | 0 |
| Escherichia coli K12 OUT 8401 | 0 | 0 |
| Escherichia coli IFO 3301 | 0 | 0 |
| Proteus vulgaris Ox$_{19}$RIMD | 37.00 | 6 |
| Gram positive bacteria | | |
| Staphylococcus aureus NIHJ-JCI | 0 | 0 |
| Bacillus subtilis var. niger OUT 4380 | 0 | 0 |
| Bacillus cereus IFO 3001 | 0 | 0 |
| Bacillus megaterium IFO 3003 | 29.20 | 0 |

EXAMPLE 5

Into a 100 ml flask equipped with a stirrer, reflux condenser, thermometer and dropping funnel were placed 20 ml of benzene and 6 ml (0.1 mole) of ethanolamine (EA). To the mixture was gradually added 2.3 g (0.1 mole) of sodium metal with stirring. The mixture was reacted at 5° to 10° C. for 5 hours.

After completion of the reaction, benzene was removed. To the residue were added 20 g of the polymer PCS obtained in Example 1 and 80 ml of methanol. The mixture was reacted at 60° C. for 24 hours and the resulting polymer (PCS-EA) was washed with water and methanol and dried. The yield was 22 g.

Into a 300 ml of flask were placed 20 g of PCS-EA, 20 ml of formaldehyde and 20 ml of formic acid and the mixture was reacted at 60° to 80° C. for 8 hours. After washing with water and methanol and drying, 21 g of a polymer (PCS-DA) was obtained.

Into 300 ml of flask were placed 20 g of PCS-DA, 3 g (0.012 mole) of lauryl bromide and 100 ml of ethanol and the mixture was reacted at 90° C. for 24 hours to obtain 23.2 g of the antibacterial polymer (PCS-TA).

The polymer had a formation rate of quaternary ammonium of about 88.5% by analysis with use of a solution of Bromophenol Blue (BPB) in methanol.

TEST EXAMPLE 5

The antibacterial polymer (PCS-TA) was checked for antibacterial activity with use of 20 mg thereof in the same manner as in Test Example 1. The results were shown in Table 6.

TABLE 6

| Bacteria | Survival rate (%) | |
|---|---|---|
|  | after 2 min. | after 5 min. |
| Gram negative bacteria | | |
| Pseudomonas aeruginosa IFO 3080 | 0 | 0 |
| Pseudomonas aeruginosa ATCC 10145 | 0.05 | 0 |
| Escherichia coli K12 OUT 8401 | 0 | 0 |
| Escherichia coli IFO 3301 | 0 | 0 |
| Proteus vulgaris Ox$_{19}$RIMD | 40.7 | 6 |
| Gram positive bacteria | | |
| Staphylococcus aureus NIHJ-JCI | 0 | 0 |
| Bacillus subtilis var. niger OUT 4380 | 0 | 0 |
| Bacillus cereus IFO 3001 | 0 | 0 |
| Bacillus megaterium IFO 3003 | 31.0 | 0.05 |

We claim:
1. An antibacterial polymer containing a repeating unit of the formula

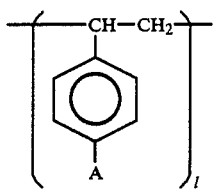
or
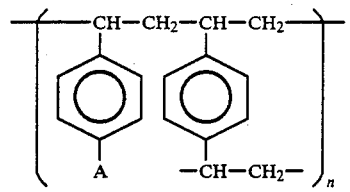
wherein A is
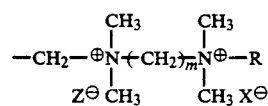
or
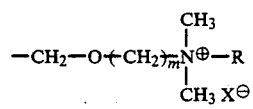
l is 20 to 2000, n is a number of at least 1000, X and Z are the same or different and are in anion, R is alkyl group having 6 to 18 carbon atoms, m is an integer of 2 to 10.
* * * * *